United States Patent
Kawasaki

(10) Patent No.: US 12,349,913 B2
(45) Date of Patent: Jul. 8, 2025

(54) LYMPHANGIOGENESIS INDUCING DEVICE

(71) Applicant: Terumo Kabushiki Kaisha, Tokyo (JP)

(72) Inventor: Manami Kawasaki, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/671,186

(22) Filed: May 22, 2024

(65) Prior Publication Data
US 2024/0307060 A1    Sep. 19, 2024

Related U.S. Application Data

(62) Division of application No. 17/541,695, filed on Dec. 3, 2021, now abandoned.

(30) Foreign Application Priority Data

Dec. 7, 2020  (JP) .................................. 2020-202523

(51) Int. Cl.
| | | |
|---|---|---|
| A61B 17/11 | (2006.01) | |
| A61B 17/34 | (2006.01) | |
| A61B 17/00 | (2006.01) | |

(52) U.S. Cl.
CPC ..... *A61B 17/11* (2013.01); *A61B 2017/00247* (2013.01); *A61B 2017/1107* (2013.01);
(Continued)

(58) Field of Classification Search
CPC . A61B 17/11; A61B 2017/1107; A61B 17/34; A61B 17/3417; A61B 2017/00247; A61B 17/3478
See application file for complete search history.

(56) References Cited

U.S. PATENT DOCUMENTS

| | | | |
|---|---|---|---|
| 3,716,058 A | | 2/1973 | Tanner |
| 4,874,375 A | * | 10/1989 | Ellison ............... A61B 17/0218 |
| | | | 604/164.01 |

(Continued)

FOREIGN PATENT DOCUMENTS

| | | |
|---|---|---|
| KR | 20140049848 A | 4/2014 |
| WO | WO-2020/162368 A1 | 8/2020 |

(Continued)

OTHER PUBLICATIONS

Suehiro et al., "Regular Compression Therapy May Not Be Necessary for Lymphedema in Arms without a Subcutaneous Echo-Free Space," Compression therapy for arm lymphedema without an echo-free space, vol. 62, Jan. 2020, pp. 258-262.

(Continued)

*Primary Examiner* — Jing Rui Ou
(74) *Attorney, Agent, or Firm* — Foley & Lardner LLP

(57) ABSTRACT

A method of forming a wound for inducing lymphangiogenesis includes: providing a lymphangiogenesis inducing device that includes: a puncture member including a distal end portion configured to puncture living tissue, and a through hole penetrating the puncture member along a central axis and extending from the distal end portion toward a proximal end, and a rod-shaped body inserted into the through hole and configured to be moved so as to protrude from the distal end portion, where the rod-shaped body includes a shaft portion, and a wound imparting structure; puncturing the living tissue with the lymphangiogenesis inducing device while the rod-shaped body is located in the through hole; passing the lymphangiogenesis inducing device through a regeneration route; pulling back the puncture member while the rod-shaped body is left in the living tissue; and pulling back the rod-shaped body.

8 Claims, 10 Drawing Sheets

(52) U.S. Cl.
CPC .......... *A61B 17/34* (2013.01); *A61B 17/3417* (2013.01); *A61B 17/3478* (2013.01)

(56) References Cited

U.S. PATENT DOCUMENTS

| | | | |
|---|---|---|---|
| 5,018,530 | A | 5/1991 | Rank et al. |
| 5,342,376 | A | 8/1994 | Ruff |
| 5,980,548 | A | 11/1999 | Evans et al. |
| 7,473,232 | B2 * | 1/2009 | Teague ............... A61B 10/0266 600/570 |
| 10,786,264 | B2 | 9/2020 | Chegini et al. |
| 2002/0138098 | A1 * | 9/2002 | Black .................... A61B 17/11 606/213 |
| 2005/0256426 | A1 | 11/2005 | Brugge |
| 2007/0213634 | A1 | 9/2007 | Teague |
| 2008/0035160 | A1 | 2/2008 | Woodson et al. |
| 2008/0066765 | A1 | 3/2008 | Paraschac et al. |
| 2008/0215072 | A1 | 9/2008 | Kelly |
| 2010/0305566 | A1 * | 12/2010 | Rosenblatt ............ A61B 46/00 606/49 |
| 2014/0171946 | A1 | 6/2014 | Benson et al. |
| 2016/0278770 | A1 | 9/2016 | Rustamova |

FOREIGN PATENT DOCUMENTS

| | | |
|---|---|---|
| WO | WO-2020/162369 A1 | 8/2020 |
| WO | WO-2020/189157 A1 | 9/2020 |

OTHER PUBLICATIONS

Office Action issued in Japanese Appl. No. 2020-202523 on Jun. 18, 2024.

* cited by examiner

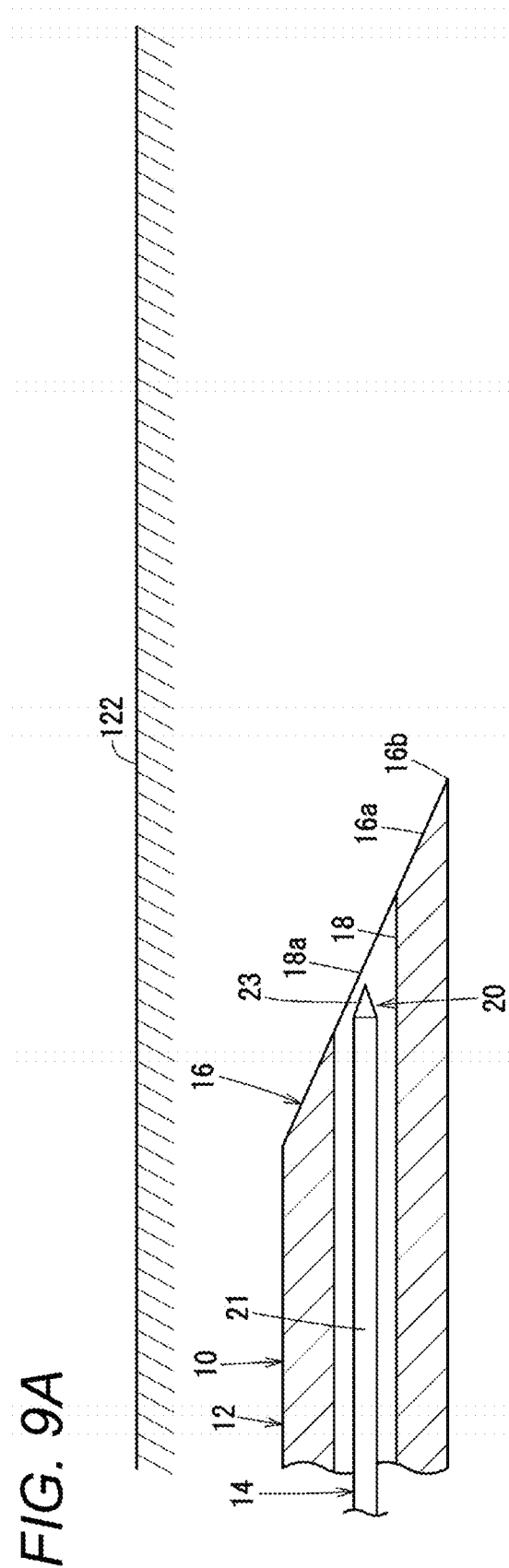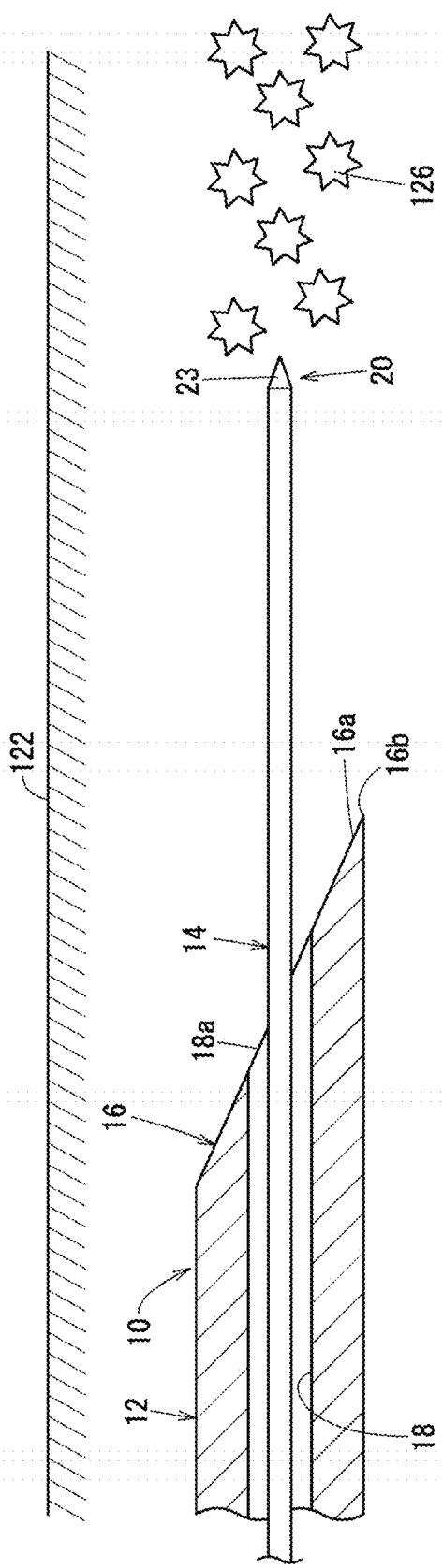

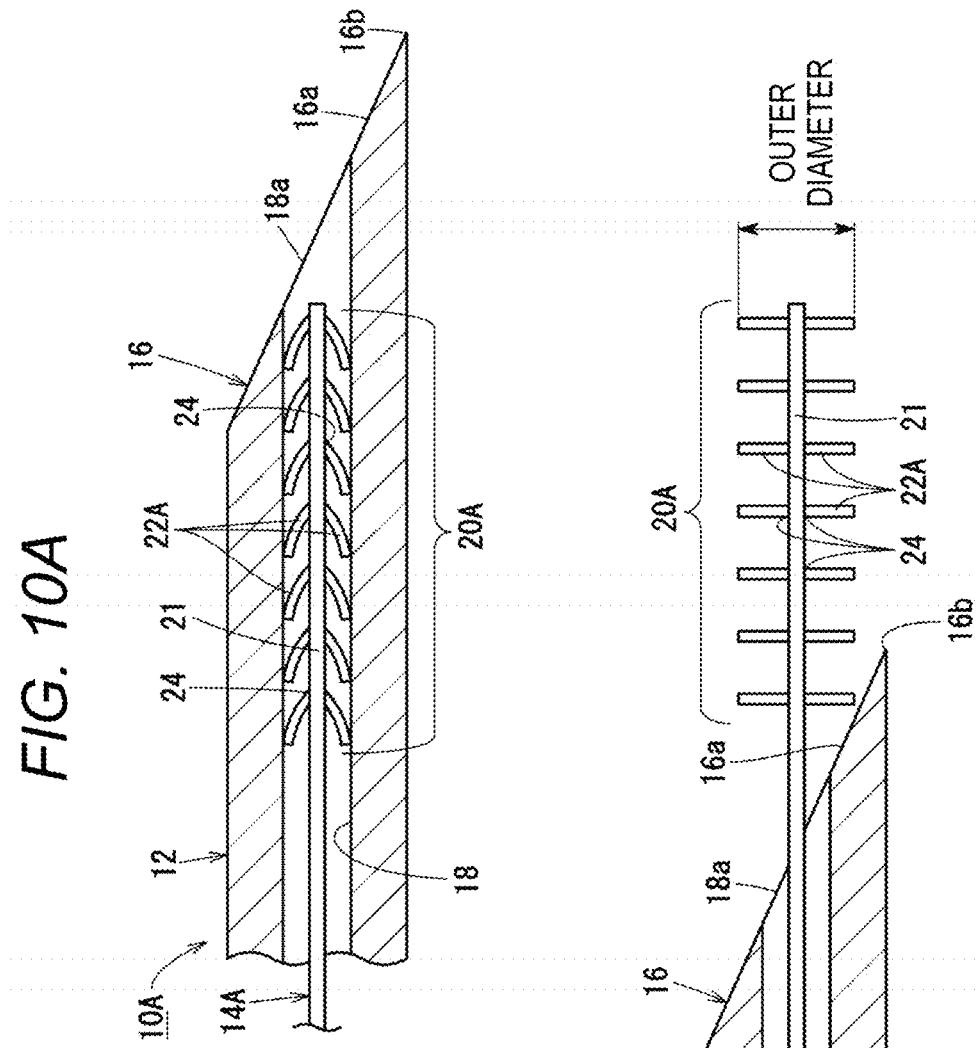

LYMPHANGIOGENESIS INDUCING DEVICE

CROSS-REFERENCE TO RELATED APPLICATION

The present application is a divisional of U.S. application Ser. No. 17/541,695, filed on Dec. 3, 2021 (now abandoned), which claims priority to Japanese Patent Appl. No. 2020-202523, filed on Dec. 7, 2020. The entire contents of these applications are incorporated by reference.

BACKGROUND

The present disclosure relates to a lymphangiogenesis inducing device used for a procedure for inducing lymphangiogenesis.

A lymphatic vessel is one route for recovering tissue fluid in a living body. When the lymphatic vessel is blocked, tissue fluid stagnates, and the limbs such as arms and legs may develop lymphedema accompanied by functional deterioration such as swelling and sensory paralysis. Lymphedema is often developed by lymph node dissection or radiation therapy performed as part of cancer treatment such as breast cancer treatment.

Lymphedema is a disease that is difficult to cure completely once it has developed. When it is chronic, it is difficult to easily improve it, and when it is left as it is, it becomes more severe.

Currently, the first choice of treatment for lymphedema is combined physical therapy ("2018 Guidelines for the Clinical Practice of Lymphedema", edited by The Japanese Lymphedema Society, pp. 81 to 83). Combined physical therapy is a treatment method in which compression therapy in which an elastic dressing, an elastic bandage, and the like are wrapped around a site where the swelling of the body occurs to impart a compression force, skin care, exercise under compression, massage, and the like are appropriately combined according to the condition of the patient (Kotaro Suehiro, Ann Vasc Surg. 2020 January; 62:258-262).

In addition, a radical treatment method of lymphedema includes lymphaticovenular anastomosis (LVA). Lymphaticovenular anastomosis is a procedure in which an anastomosis is performed so as to connect a blocked lymphatic vessel and a vein (Takumi Yamamoto et al., "SCIP flap transplantation for lymphedema", PEPARS, No. 150, pp. 54 to 64, 2019).

SUMMARY

Combined physical therapy is a conservative therapy mainly aimed at delaying the progression of lymphedema, and does not improve the symptoms. Therefore, daily self-care including compression is required, and there is a problem that a burden is large for the patient.

Lymphaticovenular anastomosis is considered to be a radical treatment. However, a problem with lymphaticovenular anastomosis is that advanced plastic surgical techniques are required and the opportunity to receive treatment is limited. In addition, there may be a case in which a vein or a lymphatic vessel suitable for anastomosis is not found, or a case in which a thrombus occurs in the anastomosed blood vessel, and a sufficient effect may not be obtained. Furthermore, it is said that the quality of anastomosis affects the result, and a unified procedure has not been determined. Therefore, the 2018 Guidelines for the Clinical Practice of Lymphedema (edited by The Japanese Lymphedema Society, pp. 81 to 83) states that lymphaticovenular anastomosis is only worth considering for patients who cannot bear compression and the like.

Therefore, an object of the present disclosure is to provide a lymphangiogenesis inducing device capable of performing radical treatments (such as lymphaticovenular anastomosis) without requiring a difficult procedure.

According to one aspect of the disclosure, a lymphangiogenesis inducing device includes a puncture member having a distal end portion capable of puncturing the living tissue and a through hole penetrating the puncture member along a central axis and extending from the distal end portion toward a proximal end, and a rod-shaped body inserted into the through hole and capable of protruding from the distal end portion, wherein the rod-shaped body includes a shaft portion and a wound imparting structure including at least one protrusion provided on the shaft portion and imparting a fine wound to the living tissue.

According to certain embodiment of the lymphangiogenesis inducing device, radical treatments (such as lymphaticovenular anastomosis) can be performed without a difficult procedure.

BRIEF DESCRIPTION OF DRAWINGS

FIG. 9A is a cross-sectional view of a lymphangiogenesis inducing device according to a modification of the first embodiment;

FIG. 9B is an explanatory diagram illustrating an operation of forming a wound using the lymphangiogenesis inducing device of FIG. 9A;

FIG. 10A is a cross-sectional view of a lymphangiogenesis inducing device according to the second embodiment; and FIG. 10B is a cross-sectional diagram illustrating deformation of a rod-shaped body protruding from the puncture member of FIG. 10A.

DETAILED DESCRIPTION

Hereinafter, preferred embodiments of the lymphangiogenesis inducing device of the present invention will be described in detail with reference to the accompanying drawings.

First Embodiment

Figure 1A:
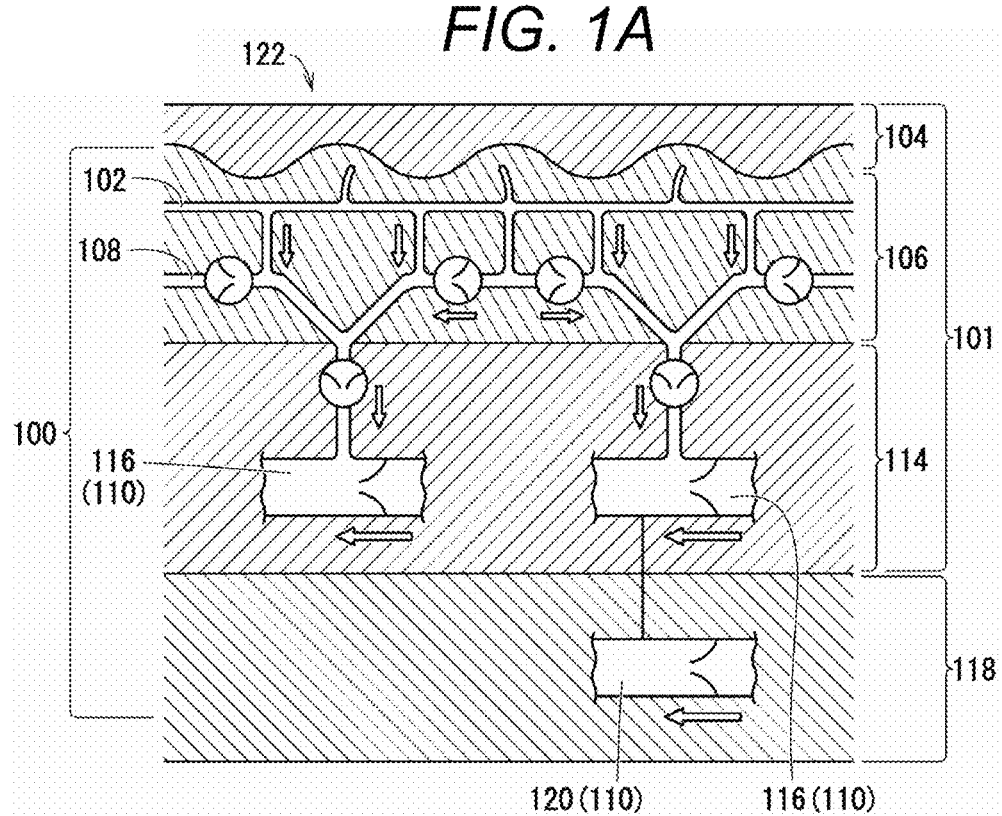
FIG. 1A is a schematic view of a normal lymphatic vessel tissue.

A lymphatic vessel tissue 100 of a normal skin 101 and a deep tissue 118 has a structure as illustrated in FIG. 1A. Lymphatic vessel tissue 100 begins in a lymphatic capillary 102. The lymphatic capillary 102 has a diameter of 20 to 70 μm and is stretched in a mesh shape in a dermis 106 immediately below an epidermis 104. The lymphatic capillary 102 transitions to a pre-collecting lymphatic vessel 108 present inside the dermis 106. The pre-collecting lymphatic vessel 108 has a diameter of 70 to 150 μm and has a valve structure in which lymphatic fluid flows from the terminal to the proximal end, and is distributed at a position deeper than the lymphatic capillary 102.

The pre-collecting lymphatic vessel 108 transitions to a collecting lymphatic vessel 110. The collecting lymphatic vessel 110 is abundant in a subcutaneous tissue 114, and has a diameter of about 0.3 mm in the upper limb and the trunk and about 0.5 mm in the lower limb. The collecting lymphatic vessel 110 has a smooth muscle around the collecting lymphatic vessel, and has a function of guiding lymphatic fluid in a central direction by the smooth muscle performing an automatic movement. The collecting lymphatic vessel 110 includes a shallow collecting vessel 116 in the subcutaneous tissue 114 and a deep collecting vessel 120 in the deep tissue 118. The shallow collecting vessel 116 and the deep collecting vessel 120 are connected to a lymph node (not illustrated) on the central side, and finally connected to a vein.

Figure 1B:
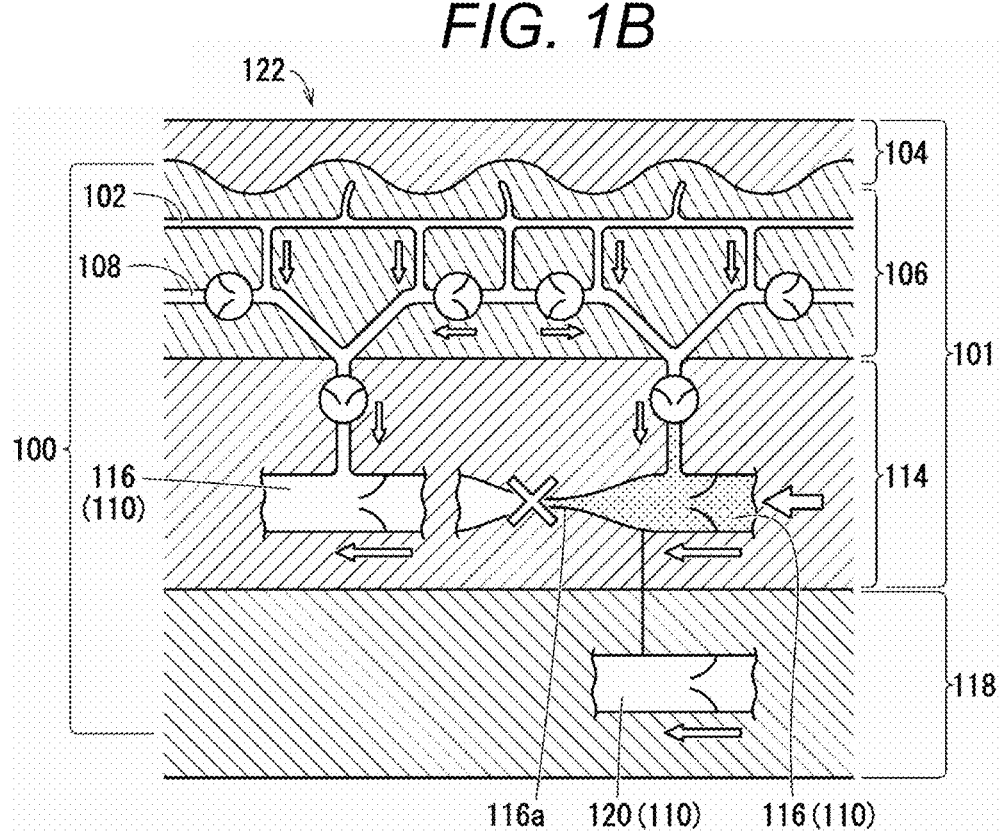
FIG. 1B is a schematic view of a lymphatic vessel tissue in which blockage has occurred in part of the lymphatic vessel.

Lymphedema is said to be caused by dysfunction of the collecting lymphatic vessel 110. As illustrated in FIG. 1B, the lymphedema is not particularly limited, but it is considered that the lymphedema is generated by generation of an occlusion site 116a mainly in the shallow collecting vessel 116. At such an occlusion site 116a, the wall of the collecting lymphatic vessel 110 thickly enlarges, and the flow path is narrowed or blocked. When the collecting lymphatic vessel 110 is blocked in this way, the tissue fluid cannot be discharged, and the limbs are swollen to develop lymphedema.

Figure 2:
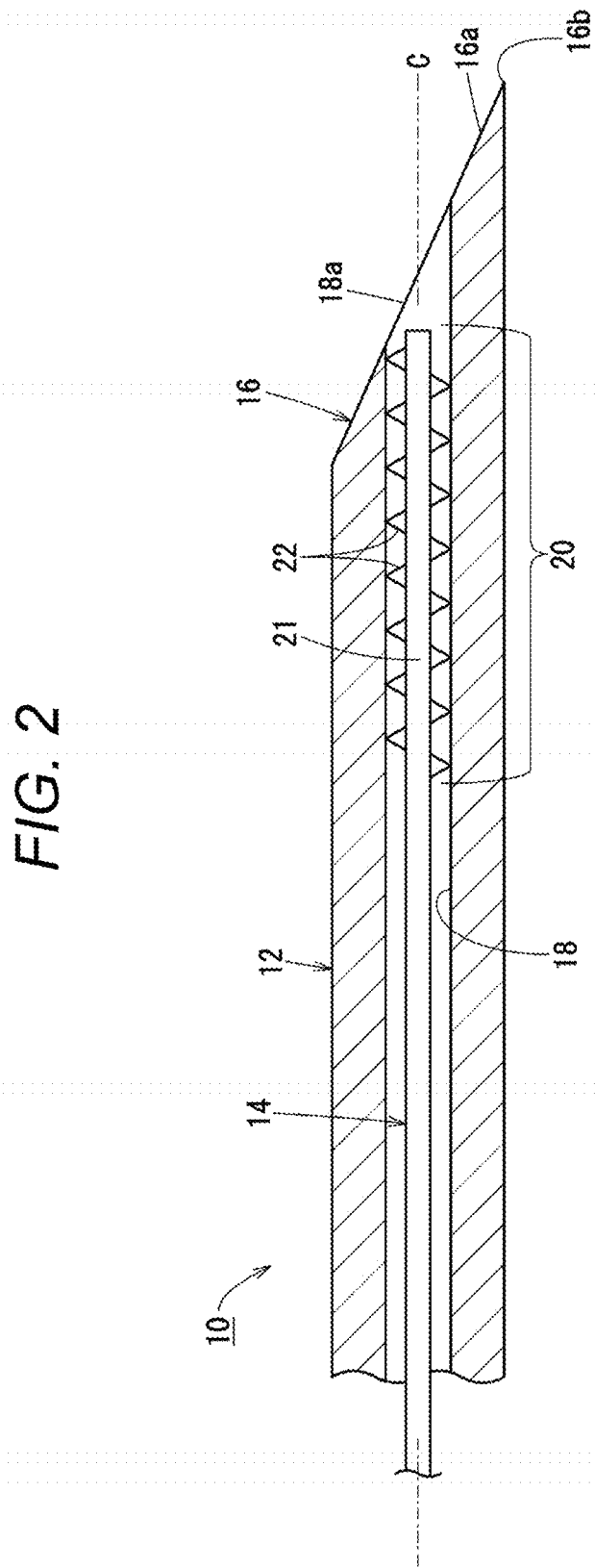
FIG. 2 is a cross-sectional view of the lymphangiogenesis inducing device according to the first embodiment.

A lymphangiogenesis inducing device 10 of the present embodiment illustrated in FIG. 2 is used for newly forming a lymphatic vessel serving as a bypass to the lymphatic vessel tissue 100 in which the above-described occlusion site 116a (see FIG. 1B) has occurred.

As illustrated, the lymphangiogenesis inducing device 10 includes a puncture member 12 and a rod-shaped body 14. The puncture member 12 is an elongated cylindrical member, and has a grip portion (not illustrated) at the proximal end. The grip portion is, for example, a cylindrical member such as a catheter hub, and an operator such as a doctor can operate the puncture member 12 by holding the grip portion.

A distal end portion 16 capable of puncturing living tissue 122 is formed at the distal end of the puncture member 12. The distal end portion 16 has, for example, an inclined face 16a obliquely cut with respect to a central axis C of the puncture member 12 as illustrated in the drawing, and a sharp needle tip 16b formed at the distal end of the inclined face 16a. The distal end portion 16 may be a blunt needle whose needle tip 16b is blunted.

A through hole 18 is formed along the central axis C inside the puncture member 12. The through hole 18 penetrates the puncture member 12 from the distal end to the proximal end. A distal end of the through hole 18 is opened in an opening 18a of the inclined face 16a. The proximal end of the through hole 18 is opened to the grip portion. The puncture member 12 and the through hole 18 are formed in a circular shape centered on the central axis C in a cross section perpendicular to the central axis C. Note that the cross-sectional shape of the puncture member 12 and the through hole 18 is not limited to a circular shape, but may be a rectangular shape or a polygonal shape.

The puncture member 12 can be formed of, for example, a metal material such as stainless steel, aluminum or an aluminum alloy, titanium or a titanium alloy, or a nickel-titanium alloy, or a material such as a hard resin or ceramics. The outer diameter of the puncture member 12 may be, for example, about 0.5 to 3.0 mm, and the inner diameter of the through hole 18 may be 0.25 to 2.5 mm.

The rod-shaped body 14 is a member whose length is about the same as or longer than the entire length of the puncture member 12, and is formed to have a size that can be inserted into the through hole 18 of the puncture member 12. The proximal end of the rod-shaped body 14 protrudes toward the grip portion of the puncture member 12. An operator such as a doctor can perform an operation of holding the proximal end of the rod-shaped body 14 and advancing and retracting the rod-shaped body 14 in the axial direction.

The rod-shaped body 14 includes a wound imparting structure 20 at a portion near the distal end. In the present embodiment, the wound imparting structure 20 includes a shaft portion 21 configured as a portion of the rod-shaped body 14 at the distal end and a plurality of protrusions 22 protruding outward from the shaft portion 21. The protrusion 22 is formed so as to protrude outward from the side portion of the shaft portion 21, and is disposed apart from each other over the entire region in the circumferential direction of the shaft portion 21. The distal end of the protrusion 22 is formed to be sharp and is formed in a shape capable of wounding the living tissue 122. The protrusion 22 may be integrally formed with the rod-shaped body 14. The shaft portion 21 can be formed to have a diameter of about 0.2 to 2.0 mm, and the protrusion 22 can have a protruding height from the shaft portion 21 of about 0.1 to 0.5 mm on average.

Although the protrusion 22 in FIG. 2 is illustrated as a plurality of protrusions randomly disposed on the outer peripheral portion of the rod-shaped body 14, the present invention is not limited thereto, and the protrusion may be spirally formed on the outer peripheral portion of the rod-shaped body 14. Further, it may be formed to protrude in a disk shape along the circumferential direction of the rod-shaped body 14. Note that the collecting lymphatic vessel 110 may extend along a nerve bundle, a blood vessel, or the like, and when the wound imparting structure 20 is too thick, the nerve bundle or the blood vessel may be damaged. In order to prevent such an event, the outer diameter of the wound imparting structure 20 (the outer diameter of the bar-shaped member including the protrusion 22) is preferably 6.0 mm or less.

The outer diameter of the rod-shaped body 14 including the protrusion 22 is formed to be smaller than the inner diameter of the through hole 18 of the puncture member 12, and the rod-shaped body 14 can smoothly advance or retract in the through hole 18. The rod-shaped body 14 including the protrusion 22 may be any material as long as it has strength capable of being inserted into the body and has hardness and toughness that can withstand abrasion with the living tissue 122. Although not particularly limited, the rod-shaped body 14 and the wound imparting structure 20 can be made of, for example, a metal material such as stainless steel, aluminum or an aluminum alloy, titanium or a titanium alloy, or a nickel-titanium alloy, or a material such as a hard resin or ceramics.

Note that the protrusion 22 may be formed by joining a member molded separately from the rod-shaped body 14 to the outer peripheral surface of the rod-shaped body 14. In this case, only the protrusion 22 may be made of a material having high hardness.

The lymphangiogenesis inducing device 10 of the present embodiment is configured as described above, and its action will be described below together with a procedure for inducing lymphangiogenesis (method of treating lymphedema).

Figure 3:
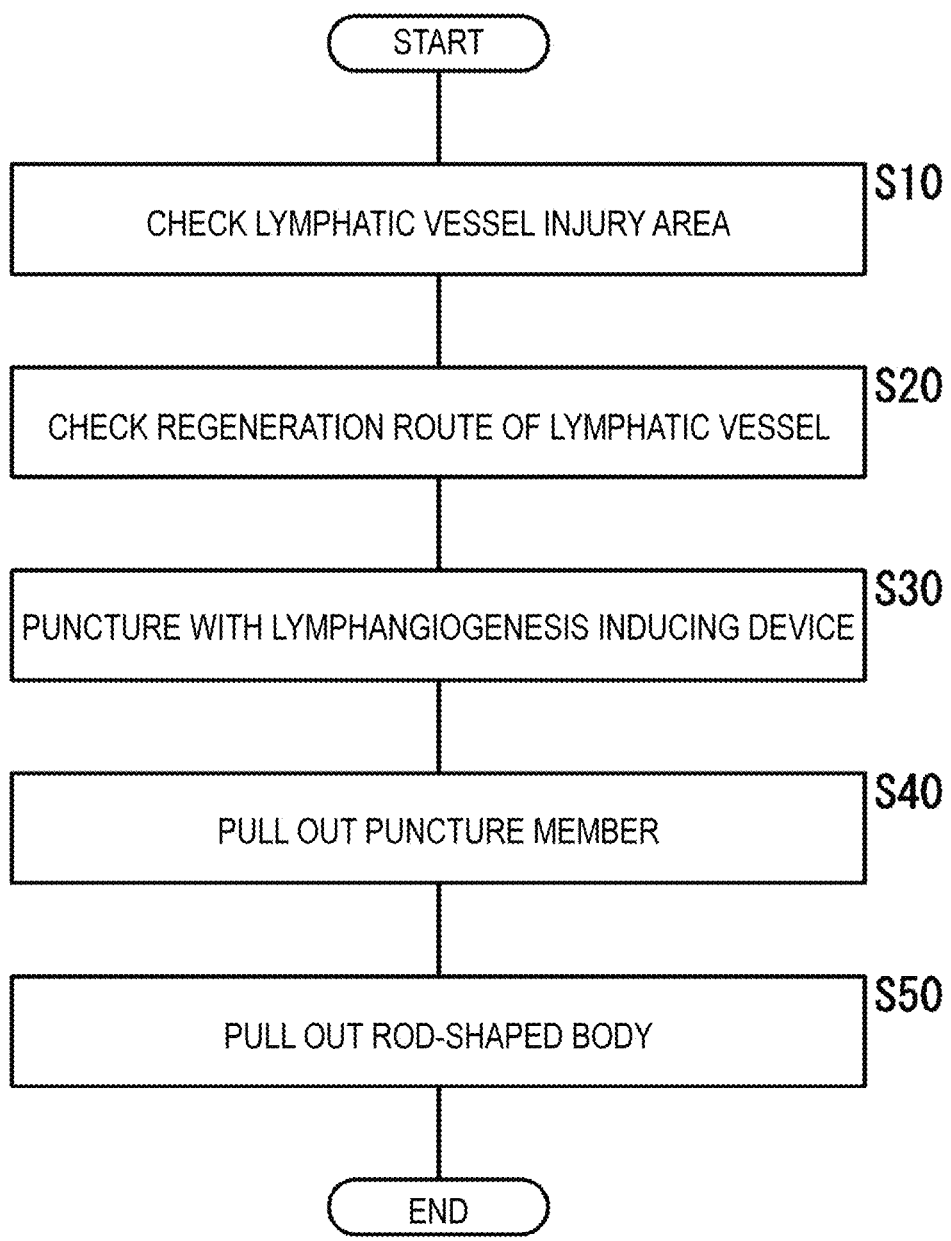
FIG. 3 is a flowchart illustrating a method of treating lymphedema using the lymphangiogenesis inducing device of FIG. 2.

As illustrated in FIG. 3, in the procedure for inducing lymphangiogenesis, first, a lymphatic vessel injury area is checked (step S10). The lymphatic vessel injury area can be checked by a method such as ICG fluorescence lymphangiography, lymphatic scintigraphy, MRI, CT, or ultrasonic image diagnosis. The ICG fluorescence lymphangiography is a method of checking lymphatic vessels by injecting ICG (indocyanine green) between fingers of a limb suffering from lymphedema and observing the flow of lymphatic fluid in or around the skin 101 with a near infrared camera. The lymphatic scintigraphy is a method of checking lymphatic vessels by injecting a liquid medicine containing a radioactive substance such as technetium into fingers of limbs and then imaging the flow of lymphatic fluid with a gamma camera.

Figure 4:
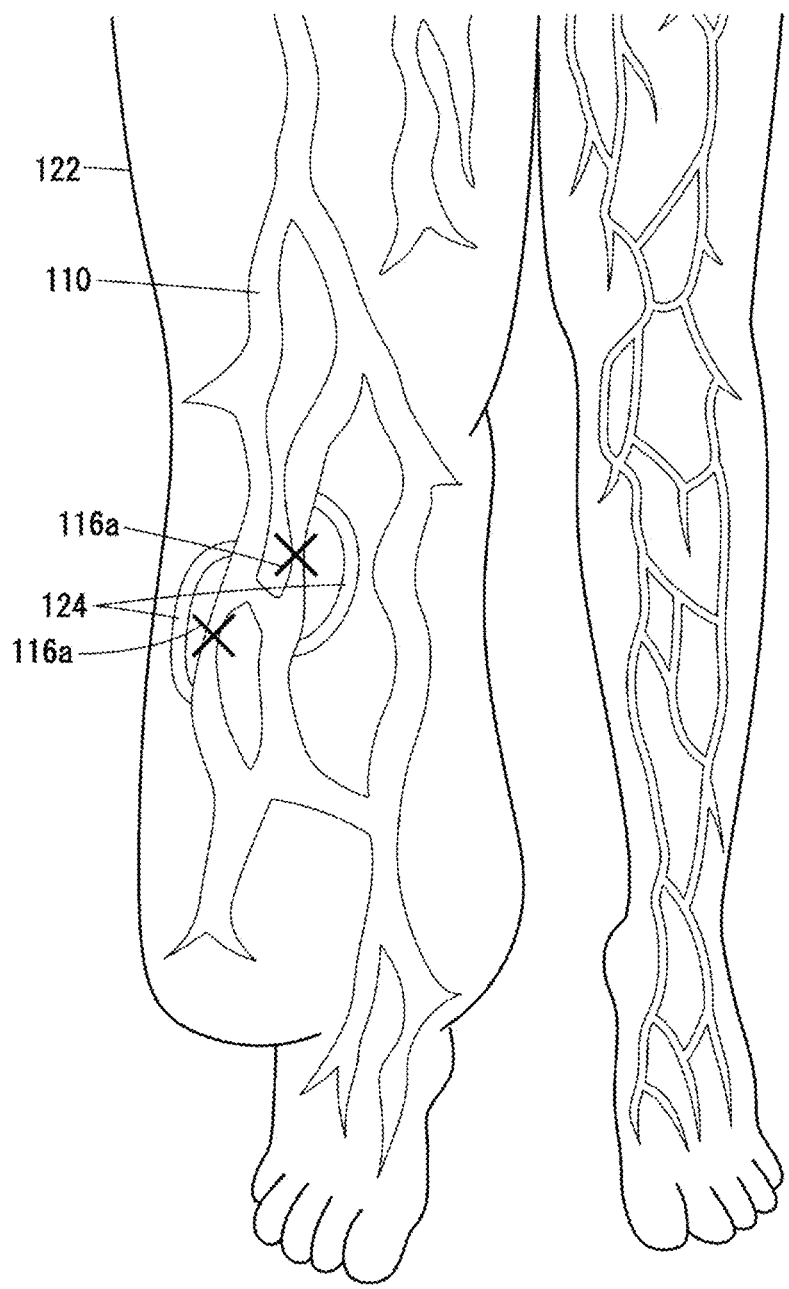
FIG. 4 is a schematic diagram illustrating an example of a regeneration route of a lymphatic vessel.

Next, a regeneration route of the lymphatic vessel is checked (step S20). Here, the blocked lymphatic vessel (for example, collecting lymphatic vessel 110) is identified, and a route 124 connecting the lymphatic vessel and the adjacent lymphatic vessel is determined. For example, in the case of FIG. 4, the route 124 bypassing the occlusion site 116*a* of the collecting lymphatic vessel 110 is determined.

Figure 5:
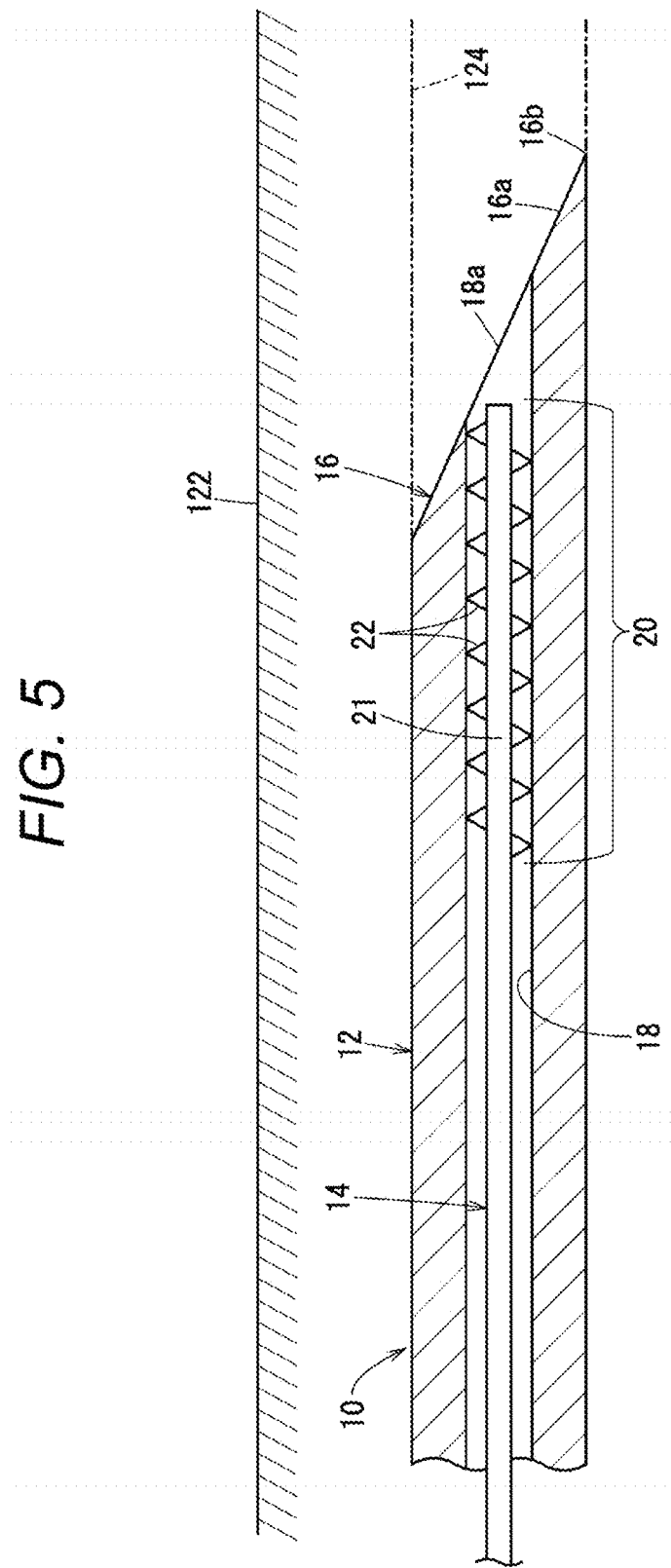
FIG. 5 is an explanatory diagram illustrating a state in which the lymphangiogenesis inducing device in FIG. 2 punctures a living tissue along a regeneration route of a lymphatic vessel in the living tissue.

Next, as illustrated in step S30 of FIG. 3, the lymphangiogenesis inducing device 10 punctures the living tissue 122. As illustrated in FIG. 5, in the lymphangiogenesis inducing device 10, the living tissue is punctured by the puncture member 12 in a state in which the rod-shaped body 14 is accommodated in the through hole 18 of the puncture member 12. Thereafter, the lymphangiogenesis inducing device 10 is advanced to pass through the portion of the route 124 in FIG. 4.

Figure 6:
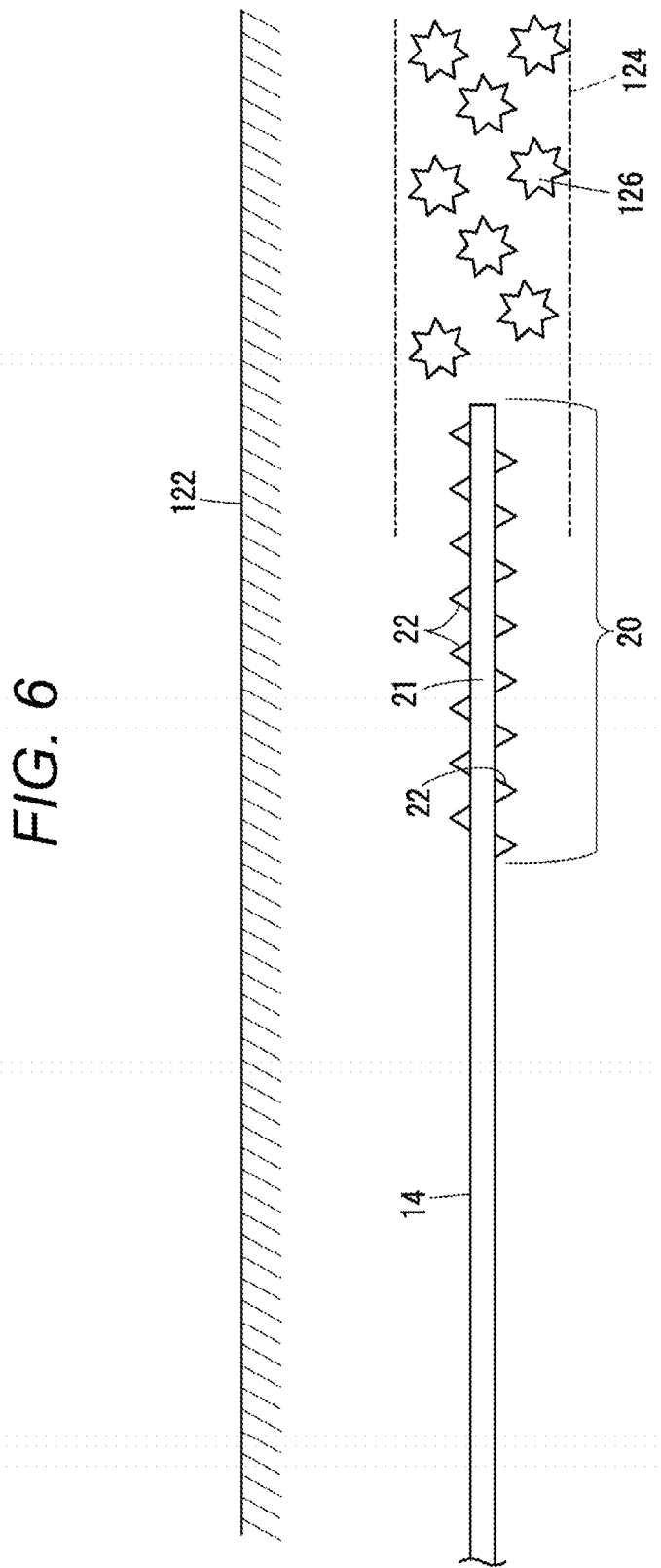
FIG. 6 is an explanatory diagram illustrating an operation of forming a fine wound in a living tissue by the lymphangiogenesis inducing device of FIG. 2.

Next, as illustrated in step S40 of FIG. 3, the puncture member 12 is pulled out from the living tissue 122. As a result, as illustrated in FIG. 6, the rod-shaped body 14 is left in the living tissue 122.

Next, as illustrated in step S50 of FIG. 3, the rod-shaped body 14 is pulled out from the living tissue 122. As illustrated in FIG. 6, when the rod-shaped body 14 is pulled out, the distal end of the protrusion 22 punctures the living tissue 122 to form a fine wound 126 in the living tissue 122. By pulling out the rod-shaped body 14, the wound 126 is formed along the route 124 of FIG. 4. Note that step S40 and step S50 in FIG. 3 are not limited to be performed separately in the illustrated order. For example, the fine wound 126 may be formed in the living tissue 122 while alternately repeating the operation of slightly pulling out the puncture member 12 (step S40) and the operation of slightly pulling out the remaining rod-shaped body 14 from the living tissue 122 (step S50). In addition, instead of pulling out the puncture member 12 from the living tissue 122 at a time, the puncture member 12 may be operated to be pulled out little by little together with the rod-shaped body 14 while maintaining the rod-shaped body 14 in a protruding state.

Thus, the procedure for one route 124 is completed. By repeating the operation of steps S10 to S50 for the other routes 124, the wounds 126 are formed for all the routes 124, and the procedure using the lymphangiogenesis inducing device 10 is completed.

Figure 7A:
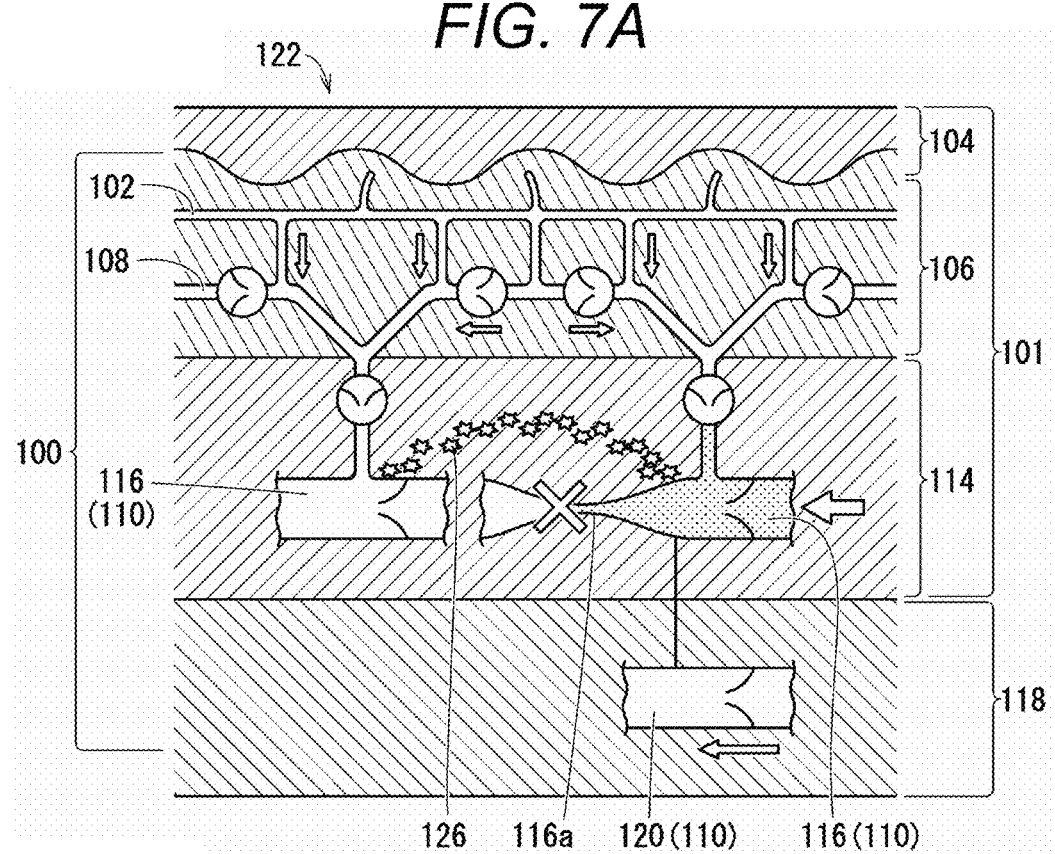
FIG. 7A is a schematic diagram illustrating a state in which a wound is formed between adjacent shallow collecting vessels by the operation of FIG. 6.

As illustrated in FIG. 7A, in the process of healing of the wound 126 along the routeway 124, immune cells accumulate in the wound 126 due to an immune reaction against the wound 126. It has been found that expression of the lymphatic growth factor is enhanced as part of immune reactions by various immune cells (Tiina P. Viitane et al., Plast Reconstr Surg Glob Open. 2013 May; 1(2):1-9). Therefore, lymphangiogenesis of the portion where the wound 126 is formed is induced by the lymphangiogenesis inducing device 10 of the present embodiment.

Figure 7B:
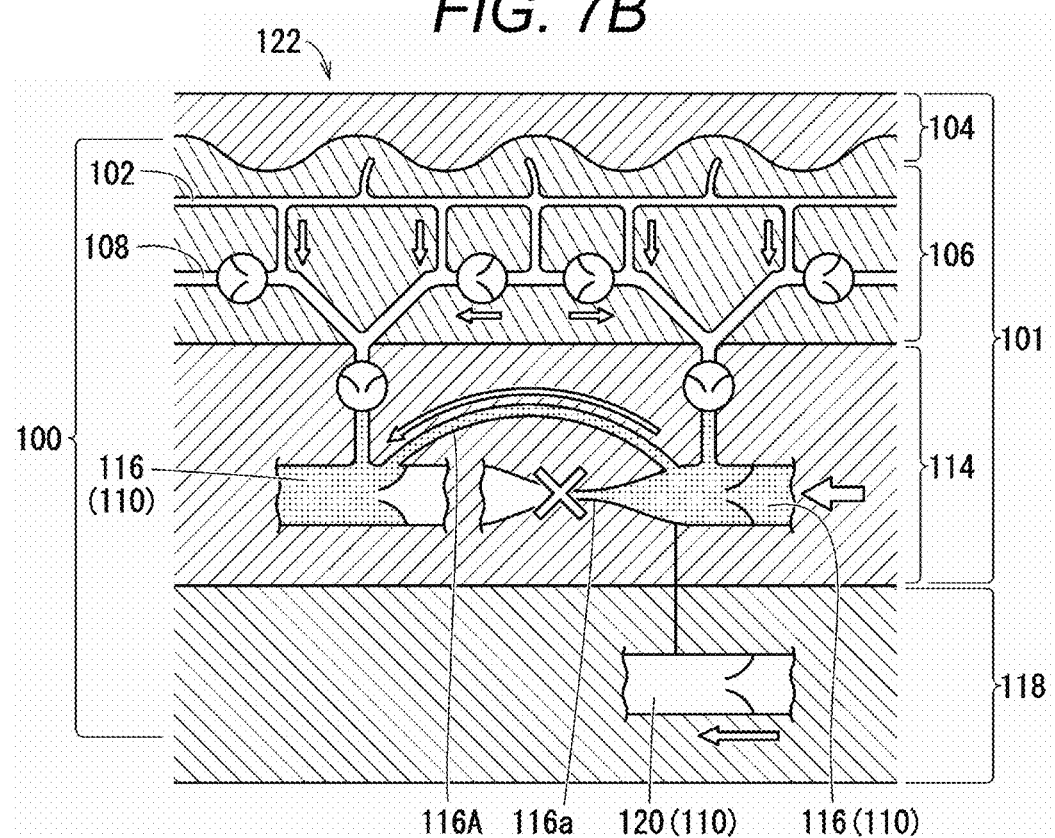
FIG. 7B is a schematic diagram illustrating a state in which a lymphatic vessel is newly generated by the wound illustrated in FIG. 7A.
Figure 8:
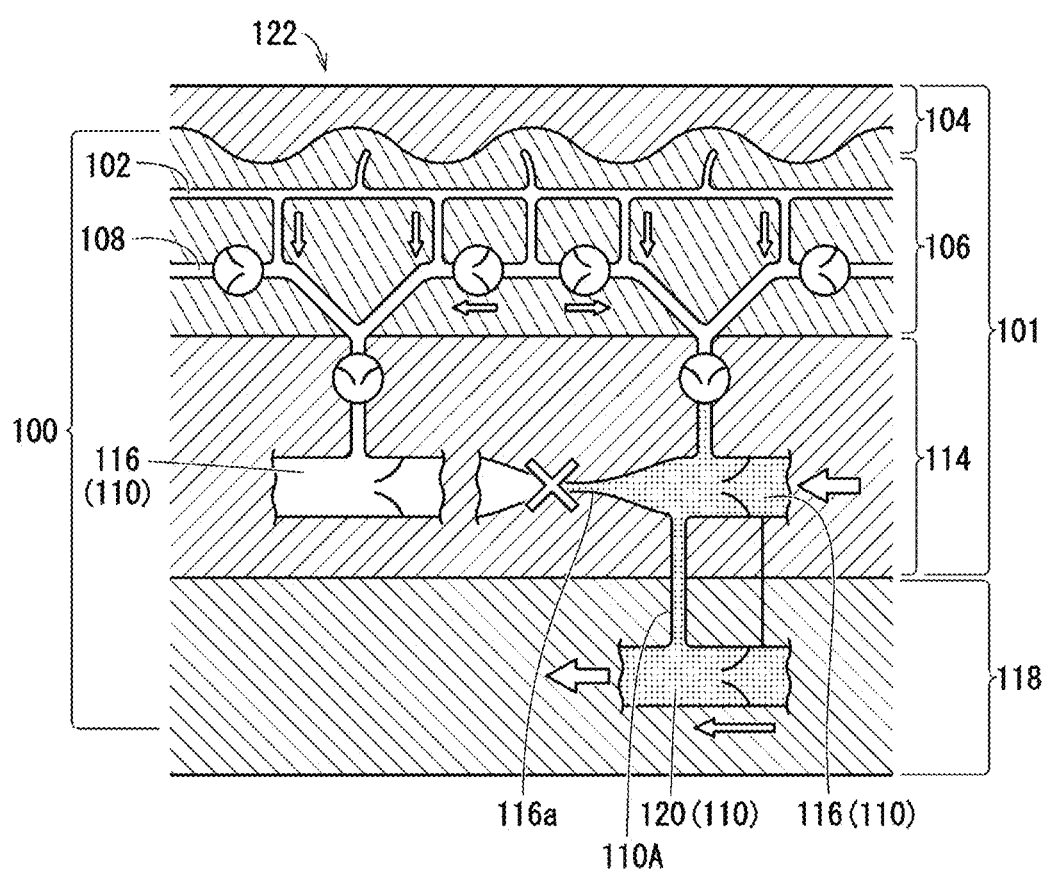
FIG. 8 is a schematic diagram illustrating a state in which a lymphatic vessel is newly generated between a shallow collecting vessel and a deep collecting vessel by the operation of FIG. 6 using the lymphangiogenesis inducing device of FIG. 2.

Lymphatic vessel neogenesis occurs as it emerges from existing lymphatic vessels (Tammela & Alitalo, Cell. 2010 Feb. 19; 140 (4): 460-476). Therefore, in the case of the wound 126 of FIG. 7A, the shallow collecting vessel 116A is newly generated so as to extend from the existing lymphatic vessel. In this way, as illustrated in FIG. 7B, a new shallow collecting vessel 116A (collecting lymphatic vessel 110) is newly generated as a bypass. As illustrated in FIG. 8, the collecting lymphatic vessel 110 newly generated by the lymphangiogenesis inducing device 10 of the present embodiment may be a collecting lymphatic vessel 110A connecting the shallow collecting vessel 116 and the deep collecting vessel 120. In addition, the puncture/operation place of the lymphangiogenesis inducing device 10 is not limited to the subcutaneous tissue. It is also possible to newly generate a new deep collecting vessel 120 connecting the deep collecting vessels 120. Furthermore, the lymphangiogenesis inducing device 10 may newly generate the lymphatic capillary 102 and the pre-collecting lymphatic vessel 108. It has been reported that the lymphatic capillary 102 and the pre-collecting lymphatic vessel 108 can also prevent the onset of lymphedema by functioning the collecting lymphatic vessel 110 as a bypass (Suami et. al., Plastic and Reconstructive Surgery, vol. 120, No. 4, pp 982-991, Sep. 15, 2007).

(Modification)

The operation using the lymphangiogenesis inducing device 10 of the present embodiment is not limited to the example described with reference to FIGS. 3 to 6. As illustrated in FIG. 9A, in the present modification, a protrusion 23 protruding in the axial direction is formed at the distal end of the rod-shaped body 14. The protrusion 23 has a sharp tip. Since the protrusion 23 has a sharp tip, a wound can be generated in the living tissue 122 torn by the tip. Further, at the proximal end of the protrusion 23, an edge may be formed at a boundary between the inclined face of the protrusion 23 and the side wall of the rod-shaped body 14. Such edges may contribute to wound generation.

In the lymphangiogenesis inducing device 10 according to this modification, the puncture member 12 punctures the vicinity of the target site in a state in which the rod-shaped body 14 is accommodated in the through hole 18 of the puncture member 12. Thereafter, as illustrated in FIG. 9B, an operation of protruding the rod-shaped body 14 from the distal end of the puncture member 12 toward the living tissue 122 is performed. As a result, the protrusion 23 of the rod-shaped body 14 punctures the living tissue 122, and the rod-shaped body 14 forms the wound 126 at the passing portion thereof. The protrusion 23 at the distal end of the rod-shaped body 14 may have a sharp shape capable of puncturing the living tissue 122 only with the rod-shaped body 14 without using the puncture member 12.

The lymphangiogenesis inducing device 10 of the present embodiment has the following effects.

The lymphangiogenesis inducing device 10 of the present embodiment includes the puncture member 12 having the distal end portion 16 capable of puncturing the living tissue 122 and the through hole 18 penetrating the puncture member 12 along the central axis C and extending from the distal end portion 16 toward the proximal end, and the rod-shaped body 14 inserted into the through hole 18 and capable of protruding from the distal end portion 16, wherein the rod-shaped body 14 includes the shaft portion 21 and the wound imparting structure 20 including at least one protrusion 22 provided on the shaft portion 21 and imparting a fine wound 126 to the living tissue 122.

According to the above configuration, since the device has the wound imparting structure 20, the fine wound 126 can be efficiently formed along the puncture route 124 of the puncture member 12. The wound 126 promotes the new generation of the lymphatic vessel, so that the new generation of the new lymphatic vessel (lymphatic capillary 102, pre-collecting lymphatic vessel 108, or collecting lymphatic vessel 110) can be promoted so as to bypass the collecting lymphatic vessel 110 that is blocked or stenosed.

In the lymphangiogenesis inducing device 10, the wound imparting structure 20 may have a plurality of protrusions 22 protruding outward from the shaft portion 21. According to this configuration, when the rod-shaped body 14 is pulled out, the plurality of protrusions 22 moves so as to tear the living tissue 122 while puncturing the living tissue 122, and thus the fine wound 126 can be efficiently formed. In addition, since the protrusion 22 can form the wound 126 in a range larger than the diameter of the rod-shaped body 14, a more active inflammatory reaction can be induced.

In the lymphangiogenesis inducing device 10 described above, the protrusions 22 may be provided at different axial positions and different circumferential positions of the shaft portion 21. According to this configuration, the fine wound 126 can be efficiently formed in the living tissue 122.

In the lymphangiogenesis inducing device 10 described above, the protrusions 22 may have the same protruding height from the shaft portion 21 in the state in which the protrusions are accommodated in the through hole 18 and in the state in which the protrusions protrude from the distal end portion 16. According to this configuration, the structure of the protrusion 22 can be simplified.

In the lymphangiogenesis inducing device 10, the protrusion 22 may be a spiral protrusion. Also with this configuration, the fine wound 126 can be efficiently formed in the living tissue 122.

In the lymphangiogenesis inducing device 10, the wound imparting structure 20 may have a configuration in which protrusion of the puncture member 12 from the distal end portion 16 and retraction of the puncture member 12 into the through hole 18 are repeatable. As a result, the operator such as a doctor can more finely operate the rod-shaped body 14, and can more finely control the position where the wound 126 is formed.

According to another aspect of the present embodiment, there is provided a treatment method using a lymphangiogenesis inducing device 10 including a puncture member 12 having a distal end portion 16 provided at a distal end and capable of puncturing a living tissue 122 and a through hole 18 penetrating the puncture member 12 along a central axis C and extending from the distal end portion 16 toward a proximal end, and a rod-shaped body 14 inserted through the through hole 18 and capable of protruding from the distal end portion 16, where the rod-shaped body 14 has a wound imparting structure 20 for imparting a fine wound 126 to the living tissue 122, wherein the treatment method includes step S30 of puncturing a living tissue 122 with the puncture member 12 along a regeneration route of a lymphatic vessel in the living tissue 122, step S40 of pulling out the puncture member 12 from the living tissue 122 while leaving the rod-shaped body 14, and step S50 of pulling out the rod-shaped body 14 from the living tissue 122.

According to the treatment method from the above viewpoint, it is possible to generate the fine wound 126 along the regeneration route of the lymphatic vessel by the wound imparting structure 20. As a result, immune cells accumulate in the wound 126 along the regeneration route of the lymphatic vessel, and the expression of the lymphatic growth factor is enhanced as part of the immune reaction by various immune cells, whereby the new generation of the lymphatic vessel can be promoted.

Second Embodiment

As illustrated in FIG. 10A, a lymphangiogenesis inducing device 10A of the present embodiment is different from the lymphangiogenesis inducing device 10 of FIG. 2 in a rod-shaped body 14A. In the lymphangiogenesis inducing device 10A of the present embodiment, the same components as those of the lymphangiogenesis inducing device 10 of FIG. 2 are denoted by the same reference numerals, and the detailed description thereof will be omitted.

As illustrated in the drawing, the rod-shaped body 14A has a wound imparting structure 20A in the vicinity of the distal end. The wound imparting structure 20A of the present embodiment includes a plurality of protrusions 22A protruding outward from the side portion of the shaft portion 21 of the rod-shaped body 14A. The protrusion 22A of the present embodiment includes the folding mechanism 24 that is deformable such that the outer end portion is folded toward the proximal end of the rod-shaped body 14A. The folding mechanism 24 of the illustrated protrusion 22A is configured by elastic deformation of the protrusion 22A. Further, the folding mechanism 24 of the protrusion 22A is not limited to the elastic deformation of the protrusion 22A, and may be configured by a hinge structure provided in the vicinity of the root of the protrusion 22A to the rod-shaped body 14A.

In a state in which the rod-shaped body 14A is accommodated in the through hole 18 of the puncture member 12, the protrusions 22A are folded, and the rod-shaped body has a size that allows insertion inside the through hole 18.

On the other hand, when the rod-shaped body 14A is protruded from the distal end portion 16 of the puncture member 12, as illustrated in FIG. 10B, the protrusion 22A is deformed to stand up and open by an elastic restoring force. As a result, the protruding range of the protrusion 22A is widened. In a state in which the protrusion 22A is opened, the protruding height of the protrusion 22A from the rod-shaped body 14A is about 0.2 to 1.0 mm in average. Therefore, in the rod-shaped body 14A of the present embodiment, the outer diameter of the wound imparting structure 20A is larger than the inner diameter of the through hole 18. The protrusion 22A is configured to maintain a standing state illustrated in FIG. 10B even when an operation of pulling out the rod-shaped body 14A toward the proximal end is performed in the living tissue 122 (see FIG. 5).

Also in the lymphangiogenesis inducing device 10A of the present embodiment, as illustrated in FIGS. 10A and 10B, an operation of forming a wound in the living tissue 122 may be performed by protruding the rod-shaped body 14A from the distal end of the puncture member 12. In this case, the rod-shaped body 14A may be reciprocated a plurality of times in the front-back direction in order to reliably unfold the protrusion 22A.

The lymphangiogenesis inducing device 10A of the present embodiment is configured as described above, and has the following effects.

The lymphangiogenesis inducing device 10A of the present embodiment has the plurality of protrusions 22A in the wound imparting structure 20A. When the protrusions 22A transition from the state in which the protrusions are accommodated in the through hole 18 to the state in which the protrusions protrude from the distal end portion 16, the protruding height from the shaft portion 21 increases.

According to this configuration, the fine wound 126 can be generated in a range larger than the inner diameter of the through hole 18. As a result, the puncture member 12 can be made thinner.

In the lymphangiogenesis inducing device 10A described above, the protrusion 22A may be folded inward in the through hole 18, and may open outward and protrude when protruding from the distal end portion 16. According to this configuration, it is possible to realize the protrusion 22A that expands larger than the inner diameter of the through hole 18 with a simple structure.

Although the present invention is described above with reference to preferred embodiments, the present invention is not limited to the above embodiments, and it goes without saying that various modifications can be made without departing from the gist of the present invention.

What is claimed is:

1. A method of forming a wound for inducing lymphangiogenesis, the method comprising:
providing a lymphangiogenesis inducing device, which comprises:
a puncture member comprising a distal end portion configured to puncture living tissue, and a through hole penetrating the puncture member along a central axis and extending from the distal end portion toward a proximal end, and
a rod-shaped body inserted into the through hole and configured to be moved so as to protrude from the distal end portion, wherein:
the rod-shaped body comprises a shaft portion, and a wound imparting structure comprising at least one protrusion located on the shaft portion and configured to impart a wound to the living tissue,
identifying a blocked lymphatic vessel;
identifying a regeneration route connecting the blocked lymphatic vessel and an adjacent lymphatic vessel;
puncturing the living tissue with the lymphangiogenesis inducing device while the rod-shaped body is located in the through hole;
passing the lymphangiogenesis inducing device through the regeneration route;
pulling back the puncture member along the regeneration route while the rod-shaped body is left in the living tissue; and
pulling back the rod-shaped body along the regeneration route such that the at least one protrusion forms a wound in the living tissue along the regeneration route.

2. The method according to claim 1, wherein:
the at least one protrusion comprises a plurality of protrusions protruding outward from the shaft portion.

3. The method according to claim 2, wherein:
the plurality of protrusions comprises protrusions located at different axial positions and different circumferential positions of the shaft portion.

4. The method according to claim 2, wherein:
the protrusions have the same protruding height from the shaft portion in a state in which the protrusions are located in the through hole and in a state in which the protrusions are located outside the through hole.

5. The method according to claim 2, wherein:
the protrusions have a protruding height from the shaft portion that increases when the protrusions transition from a state in which the protrusions are located in the through hole to a state in which the protrusions are located outside the through hole.

6. The method according to claim 5, wherein:
the protrusions are folded inward when in the state in which the protrusions are located in the through hole, and open outward and protrude when in the state in which the protrusions are outside the through hole.

7. The method according to claim 1, wherein:
the protrusion is a spiral protrusion.

8. The method according to claim 1, wherein:
the wound imparting structure has a configuration in which protrusion of the wound imparting structure from the distal end portion and retraction of the wound imparting structure into the through hole are repeatable.

* * * * *